United States Patent
Vargas et al.

(10) Patent No.: US 10,482,183 B1
(45) Date of Patent: Nov. 19, 2019

(54) DEVICE AND METHOD FOR NATURAL LANGUAGE PROCESSING THROUGH STATISTICAL MODEL COMPARISON

(71) Applicant: Babylon Partners Limited, London (GB)

(72) Inventors: Francisco Vargas, London (GB); Kamen Brestnichki, London (GB); Dane Grant Sherburn, London (GB); Vitalii Zhelezniak, London (GB); Nils Yannick Hammerla, London (GB)

(73) Assignee: Babylon Partners Limited, London (GB)

( * ) Notice: Subject to any disclaimer, the term of this patent is extended or adjusted under 35 U.S.C. 154(b) by 0 days.

(21) Appl. No.: 16/144,718

(22) Filed: Sep. 27, 2018

(51) Int. Cl.
*G10L 15/22* (2006.01)
*G06F 17/27* (2006.01)
*G06F 17/28* (2006.01)
*G06N 7/00* (2006.01)

(52) U.S. Cl.
CPC .......... *G06F 17/2785* (2013.01); *G06F 17/28* (2013.01); *G06N 7/005* (2013.01); *G10L 15/22* (2013.01)

(58) Field of Classification Search
CPC combination set(s) only.
See application file for complete search history.

(56) References Cited

U.S. PATENT DOCUMENTS

2018/0276134 A1* 9/2018 Cherubini ........... G06F 12/0888

OTHER PUBLICATIONS

Anonymous authors, "Model Comparison for Semantic Grouping" under review as a conference paper at ICLR 2019, pp. 1-6.
Eneko A., et al., SemEval-2012 task 6: A pilot on semantic textual similarity. Proceedings of the First Joint Conference on Lexical and Computational Semantics—vol. 1: Proceedings of the main conference and the shared task, and vol. 2: Proceedings of the Sixth International Workshop on Semantic Evaluation. pp. 385-393.
Eneko , A., et al., *Sem 2013 shared task: Semantic textual similarity. Second Joint Conference on Lexical and Computational Semantics (*SEM), vol. 1: Proceedings of the Main Conference and the Shared Task, pp. 32-43, Atlanta, Georgia, Jun. 13-14, 2013.

(Continued)

*Primary Examiner* — Abul K Azad
(74) *Attorney, Agent, or Firm* — McDermott Will & Emery LLP

(57) ABSTRACT

A computer-implemented method comprising: receiving the first set of words and the second set of words, wherein each of the first and second sets of words; calculating a first likelihood-based measure representing how well a first model can be fit to the first and second sets of words, the first model comprising a shared parametric distribution representing both the first and second sets of words; calculating a second likelihood-based measure representing how well a second model can be fit to the first and second sets of words, the second model comprising a first parametric distribution representing the first set of words and a second parametric distribution representing the second set of words; calculating a similarity score based on a ratio of the first likelihood measure to the second likelihood measure, the similarity score being representative of the similarity between the first and second sets of words; and outputting the similarity score.

17 Claims, 5 Drawing Sheets

(56) References Cited

OTHER PUBLICATIONS

Eneko, A., et al., SemEval-2014 task 10: Multilingual semantic textual similarity. Proceedings of the 8th International Workshop on Semantic Evaluation (SemEval 2014), pp. 81-91, Dublin, Ireland, Aug. 23-24, 2014.
Eneko, A., et al., SemEval-2015 task 2: Semantic textual similarity, English, Spanish and pilot on Interpretability. Proceedings of the 9th International Workshop on Semantic Evaluation (SemEval 2015), pp. 252-263, Denver, Colorado, Jun. 4-5, 2015.
Eneko, A., et al., SemEval-2016 task 1: Semantic textual similarity, Monolingual and Cross-Lingual Evaluation. In Proceedings of the 10th International Workshop on Semantic Evaluation (SemEval-2016), pp. 497-511, 2016.
Hirotugu Akaike. A new look at the statistical model identification. IEEE transactions on automatic control, vol. 19, No. 6:716-723, 1974.
Hirotugu, A., et al. Likelihood of a model and information criteria. Journal of econometrics, vol. 16, Issue 1:3-14, 1981.
Sanjeev, A., A simple but tough-to-beat baseline for sentence embeddings. International Conference on Learning Representations, 2017.
Athiwaratkun, B., et al., Multimodal word distributions. http://aclweb.org/anthology/P17-1151.
Banerjee, A., et al., Clustering on the Unit Hypersphere using von Mises-Fisher Distributions. Journal of Machine Learning Research, vol. 6: 1345-1382, 2005.
Berger, J., et al., Bayesian analysis: A look at today and thoughts of tomorrow. Journal of the American Statistical Association, 95(452):1269-1276, 2000. ISSN 01621459. URL http://www.jstor.org/stable/2669768.
Bird, S., et al., Natural language processing with Python: analyzing text with the natural language toolkit. "O'Reilly Media, inc.", 2009.
Blacoe, W., et al., A comparison of vector-based representations for semantic composition. Proceedings of the 2012 Joint Conference on Empirical Methods in Natural Language Processing and Computational Natural Language Learning, pp. 546-556, Jeju Island, Korea, Jul. 12-14, 2012.
Dziak, J., et al., Sensitivity and specificity of information criteria. The Methodology Center and Department of Statistics. Penn State, The Pennsylvania State University. 16(30):140, 2012. https://methodology.psu.edu/media/techreports/12-119.pdf.
Fisher, N., et al., Statistical analysis of spherical data. Cambridge university press. Jan. 2010. https://doi.org/10.1017/CBO9780511623059.
Ghahramani, Z., et al., Bayesian sets. In Advances in neural information processing systems, pp. 435-442. (NIPS 2005).
Kiros, R., et al., Skip-Thought Vectors. URL https://arxiv.org/abs/1506.06726.
Konishi, S., et al., Information criteria and statisrical modeling. Springer Science & Business Media, 2008. ISBN 978-0-387-71887-3.
Zheng, G., et al., Learning to Reweight terms with distributed representations. SIGIR '15 Proceedings of the 38th International ACM SIGIR Conference on Research and Development in Information Retrieval. pp. 575-584. Santiago, Chile, Aug. 2015. https://dl.acm.org/citation.cfm?id=2767700.
Kusner, M., et al., From word embeddings to document distances. Proceedings of the 32nd International Conference on Machine Learning, Lille, France, 2015. JMLR: W&CP vol. 37.
Bartlett, S.M., A Comment on D.V. Lindley's statistical paradox. Biometrika, 44(3/4): 533-534, 1957.
Mardia K.V., et al. Distribution Theory for the Von Mises-Fisher Distribution and Its Application. In A Modern Course on Statistical Distributions in Scientific Work. NATO Advanced Study Institutes Series (Series C—Mathematical and Physical Sciences), vol. 17. Springer, Dordrecht (1975).
Marshall, P., et al., Bayesian evidence as a tool for comparing datasets, Physical Review D, vol. 73, Issue 6. Mar. 2006.
Mikolov, T., et al., Distributed representations of words and phrases and their compositionality. Proceeding NIPS'13 Proceedings of the 26th International Conference on Neural Information Processing Systems—vol. 2 pp. 3111-3119 Lake Tahoe, Nevada Dec. 2013.
Mitchell, J., et al., Vector-based Models of Semantic Composition. Proceedings of ACL-08: Association for Computational Linguistics. pp. 236-244. 2008. http://aclweb.org/anthology/P08-1028.
Mitchell, J., et al., Composition in Distributional Models of Semantics. Cognitive science, 34(8): 1388-1429. 2010.
Pennington, J., et al., Glove: Global vectors for word representation. Proceedings of the 2014 Conference on Empirical Methods in Natural Language Processing (EMNLP), Association for Computational Linguistics, pp. 1532-1543, 2014. http://aclweb.org/anthology/D14-1162.
Gideon Schwarz et al. Estimating the Dimension of a Model. The Annals of statistics, vol. 6, No. 2. pp. 461-464, Mar. 1978. https://www.jstor.org/stable/2958889.

* cited by examiner

DEVICE AND METHOD FOR NATURAL LANGUAGE PROCESSING THROUGH STATISTICAL MODEL COMPARISON

TECHNICAL FIELD

The present disclosure relates to improvements in computational efficiency and accuracy of determining semantic similarity between input text, and in particular, between input text encoded using distributed vector representations located in a learned embedding space using a calculated Bayes factor indicative of model generation similarity or dissimilarity.

BACKGROUND

Natural language processing and dialogue system, such as chatbots, are now becoming commonplace in many fields. Natural language processing relates to how computers process and analyse natural language data. Dialogue systems (or conversational agents) are computer systems intended to converse with humans in a coherent manner. Naturally, such systems are heavily dependent on their accuracy in recognising input text.

Whilst dialogue systems have become more effective in recent years, such systems are not perfect. The ramifications of giving an incorrect answer by a dialogue system to a question relating to directions or re-directing a call in an automated computer system are annoying, but unlikely to cause serious distress.

There is a much larger challenge to implement a dialogue system in a medical setting as incorrect advice could potentially have disastrous results. For this reason, dialogue systems that are deployed to give medical information are strictly controlled to give advice that is validated by a medical professional. Having said this, a user of a medical dialogue system may express their symptoms in many different ways and the validation by a medical professional must be able to cover all inputs. Also, validation by a medical expert is a long process and repetition of the validation process should be minimised.

There is therefore a need for improve natural language processing, particularly in the field of dialogue systems for providing medical information.

SUMMARY

Embodiments described herein provide computer implemented methods and systems for determining a statistical measure for the semantic textual similarity between two sets of input words. Determining the semantic textual similarity is important for natural language processing systems. For instance, a dialogue system may be able to recognise an input phrase based on the similarity between the input phrase and a set of predefined input phrases.

The embodiments described herein provide more effective and efficient means of determining the similarity between two sets of words. For instance, embodiments described herein can computed in linear time (computational complexity in the order of O(nd), where n is the number of words in the sets and d is the number of parameters in the parametric distributions. This is in contrast to alternative methods that have higher order computational complexity (e.g. $O(n^2 d)$ or $O(nd^3)$). Furthermore, the methods described herein can be implemented in real-time for comparison of any combination of words without requiring the system to be trained in advance.

According to a first aspect there is provided a computer-implemented method. The method comprises receiving the first set of words and the second set of words, wherein each of the first and second sets of words. The method further comprises calculating a first likelihood-based measure representing how well a first model can be fit to the first and second sets of words, the first model comprising a shared parametric distribution representing both the first and second sets of words, and calculating a second likelihood-based measure representing how well a second model can be fit to the first and second sets of words, the second model comprising a first parametric distribution representing the first set of words and a second parametric distribution representing the second set of words. The method further comprises calculating a similarity score based on a ratio of the first likelihood measure to the second likelihood measure, the similarity score being representative of the similarity between the first and second sets of words and outputting the similarity score.

Embodiments described herein determine the similarity between two words via a similarity score that determines the goodness of fit for a first model that models the two sets of words via a shared parametric distribution relative to the goodness of fit for a second model that models the two sets of words via two independent parametric distributions. This formulates the similarity problem as a model comparison problem. This is on the basis that similar sets of words are more likely to be able to be generated from a single distribution (encoding the semantic similarity) whereas non-similar sets of words are more accurately represented by independent distributions. In the latter situation, the first set of words can be modelled via the first probability distribution whereas the second set of words can be modelled via the second probability distribution.

The first and second sets of words may be in the form of word embeddings. These word embeddings may be received by the system from an external source, or may be calculated by the system and provided for use in determining the similarity. By operating in word embedding space, embodiments may become more efficient and effective by making use of the semantic meaning encoded within the embeddings.

The similarity score can be determined by determining the ratio of the first likelihood measure to the second likelihood measure. This may be obtained via division (where the likelihood-based measures are calculated in a linear scale) or subtraction (where the likelihood-based measures are calculated in a logarithmic scale). The first and second likelihood-based measures may be calculated before the similarity score is calculated. Alternatively, the first and second likelihood-based measures may be calculated as part of the calculation of the similarity score (i.e. in one step).

The likelihood-based measures can be considered measures of the goodness of fit of the respective model to the first and second sets of words. For the second likelihood-based measure, this may be reflective of the goodness of fit of the first parametric distribution to the first set of words and the goodness of fit of the second parametric distribution to the second set of words.

According to a further embodiment, the first, second and shared parametric distributions are first, second and shared likelihood functions respectively, each defined by a respective set of parameters. These functions therefore provide the likelihood of a given set of parameters given the respective set or sets of words. For instance, the shared likelihood distribution represents the likelihood of a set of parameters given the first and second sets of words, whilst the first and second likelihood distributions represent the likelihood of respective sets of parameters given the first and second sets of words respectively. The likelihood functions may be in a linear scale or a logarithmic scale. That is, the likelihood functions may be log-likelihood functions.

According to one embodiment the first model comprises a shared set of parameters that describe the shared parametric distribution and the second model comprises first and second sets of parameters, the first set of parameters describing the first parametric distribution and the second set of parameters describing the second parametric distribution.

According to a further embodiment the first and second sets of words are first and second sets of word embeddings constrained to lie on the surface of a unit hypersphere, and the first, second and shared likelihood functions are in accordance with the von Mises-Fisher distribution.

Constraining the word embeddings to lie on a unit hypersphere simplifies the calculation of the similarity score. Furthermore, the von Mises-Fisher distribution is well suited to use with spherical embeddings. The word embeddings may be represented in polar coordinates. The system may receive or calculate the word embeddings in the required format, or may convert received (or otherwise calculated) word embeddings into polar coordinates.

For instance, in one embodiment the first and second likelihood-based measures are information criteria (for instance, the Takeuchi Information Criterion) that involve the calculation of the Hessian and empirical Fisher information matrix. The use of word embeddings on the unit hypersphere (e.g. in polar coordinates) simplifies the calculation of the Hessian and Fisher information matrices.

According to a further embodiment the method further comprises determining maximum likelihood estimates for the parameters for each likelihood function. This allows the determination of the best fit models according to the input words.

According to one embodiment the maximum likelihood estimate for each likelihood function is based on the set or sets of words to which the function relates. For instance, the maximum likelihood estimate for the shared likelihood function may be determined based on the first and second sets of words, whilst the maximum likelihood estimates for the first and second likelihood functions may be determined based on the first set of words and the second set of words respectively. The maximum likelihood estimates can be considered the values of the parameters that maximise the respective parametric distribution (likelihood function).

According to an embodiment the first likelihood-based measure is calculated based on a maximum value for the shared likelihood function and the second likelihood-based measure is calculated based on maximum values for the first and second likelihood functions. The maximum value can be considered the value of the respective parametric distribution/likelihood function at the maximum likelihood estimates of the parameters for that distribution.

According to a further embodiment the first and second likelihood based measures are first and second information criteria respectively. These provide means for selecting the best-fitting model. Accordingly, information criteria provide a measure for how well a respective model fits input data (the goodness of fit).

According to an embodiment the first and second information criteria are in accordance with the Takeuchi Information Criterion or the Akaiki Information Criterion. These have been found to be effective methods of measuring the goodness of fit, particularly for use in determining the similarity between two sets of words.

According to a further embodiment the first and second likelihood-based measures each comprise a respective penalty based on complexity for the respective model. This helps avoid the method overfitting the models, thereby providing a more accurate method for determining the similarity between the two sets of words.

According to a further aspect there is provided a system for determining similarity between a first set of words and a second set of words, the system comprising one or more processors configured to: receive the first set of words and the second set of words, wherein each of the first and second sets of words; calculate a first likelihood-based measure representing how well a first model can be fit to the first and second sets of words, the first model comprising a shared parametric distribution representing both the first and second sets of words; calculate a second likelihood-based measure representing how well a second model can be fit to the first and second sets of words, the second model comprising a first parametric distribution representing the first set of words and a second parametric distribution representing the second set of words; calculate a similarity score based on a ratio of the first likelihood measure to the second likelihood measure, the similarity score being representative of the similarity between the first and second sets of words; and output the similarity score.

According to an embodiment the first, second and shared parametric distributions are first, second and shared likelihood functions respectively, each defined by a respective set of parameters.

According to an embodiment the first and second sets of words are first and second sets of word embeddings constrained to lie on the surface of a unit hypersphere, and wherein the first, second and shared likelihood functions are in accordance with the von Mises-Fisher distribution.

According to an embodiment the one or more processors are further configured to determine maximum likelihood estimates for the parameters for each likelihood function.

According to an embodiment the first likelihood-based measure is calculated based on a maximum value for the shared likelihood function and the second likelihood-based measure is calculated based on respective maximum values for the first and second likelihood functions.

According to an embodiment the first and second likelihood based measures are first and second information criteria respectively.

According to an embodiment the first and second information criteria are in accordance with the Takeuchi Information Criterion or the Akaiki Information Criterion.

According to an embodiment the first and second likelihood-based measures each comprise a respective penalty based on complexity for the respective model.

According to a further aspect there is provided a non-transient computer readable medium containing programming instructions that, when executed by a computer, cause the computer to: receive the first set of words and the second set of words, wherein each of the first and second sets of words; calculate a first likelihood-based measure representing how well a first model can be fit to the first and second sets of words, the first model comprising a shared parametric distribution representing both the first and second sets of words; calculate a second likelihood-based measure representing how well a second model can be fit to the first and second sets of words, the second model comprising a first parametric distribution representing the first set of words and a second parametric distribution representing the second set of words; calculate a similarity score based on a ratio of the first likelihood measure to the second likelihood measure, the similarity score being representative of the similarity between the first and second sets of words; and output the similarity score.

Accordingly, the methods described herein may be embodied in various forms including systems and non-transient computer readable media.

BRIEF DESCRIPTION OF THE DRAWINGS

Arrangements of the present invention will be understood and appreciated more fully from the following detailed description, made by way of example only and taken in conjunction with drawings in which.

DETAILED DESCRIPTION

Figure 1:
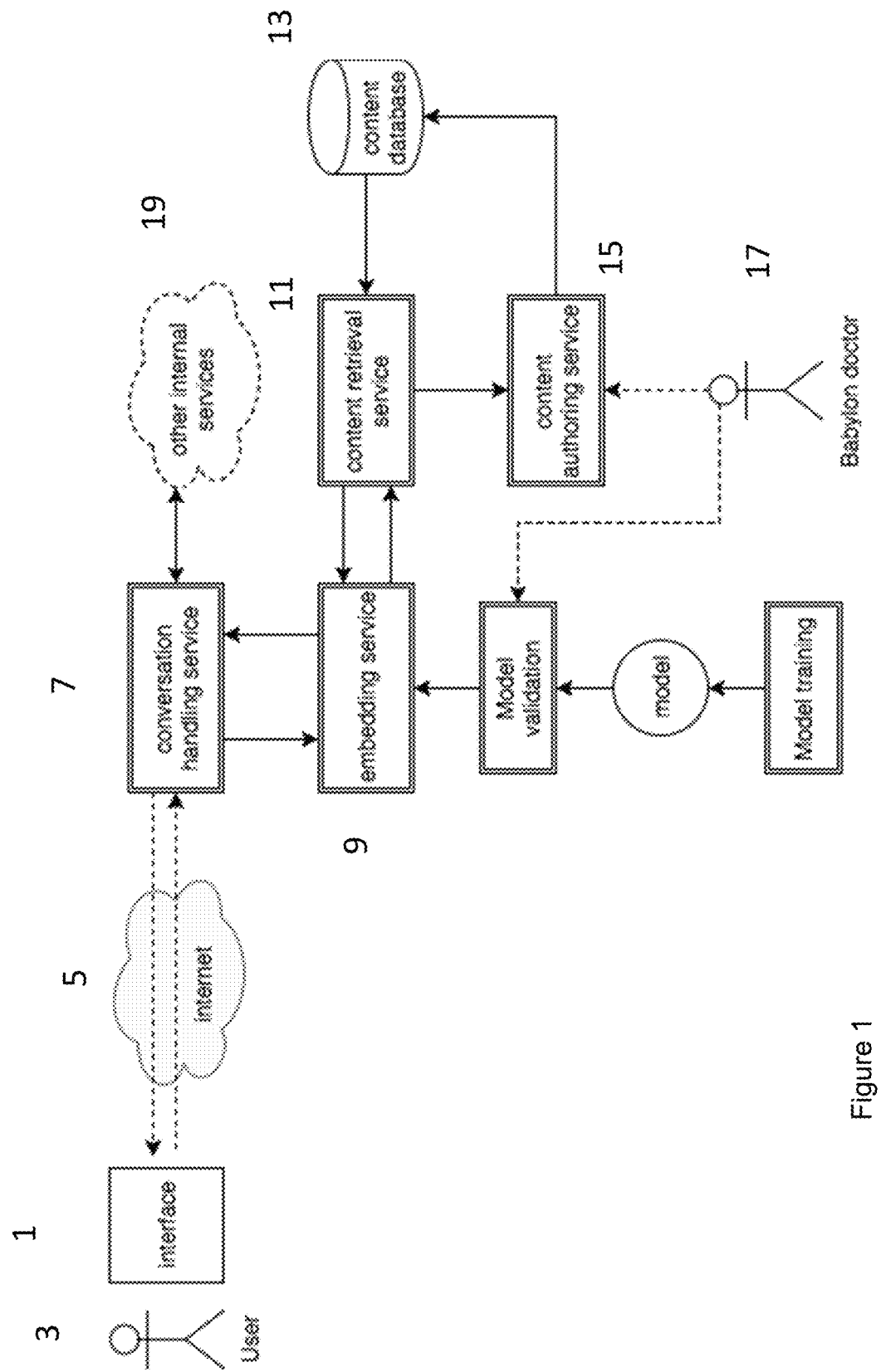
FIG. 1 shows a system in accordance with a first embodiment.

This specification relates to improvements in computational efficiency and accuracy of determining semantic similarity between input text, and in particular, input text encoded using distributed vector representations located in a learned embedding space using a calculated Bayes factor indicative of model generation similarity or dissimilarity.

Recent progress in word embeddings has allowed the encoding of words using distributed vector representations that capture semantic information through their location in the learned embedding space. However a technical problem still remains. Particularly, use of these representations to express semantic grouping between documents, sentences and other textual formats, is a technical problem because current methods are computationally complex and inefficient, and often require models to be fit to labelled training data in advance. It is often difficult and expensive to obtain the large amounts of training data required to effectively fit models to the data, and this also offers reduced flexibility as only predefined sets of words may be considered.

The compositional nature of distributed representations indicates the presence of semantic grouping in these representation spaces. Under this setting the task of semantic similarity can be formulated as an inference task: "are two arbitrary subsets of words partitions of the same semantic group?"

Embodiments described herein provide a technical solution to the above technical problem. Specifically, embodiments described herein formulate the task of semantic similarity between two arbitrary sets of objects as a Bayesian model comparison problem. A score is provided based on the calculation of a Bayes factor that indicates how likely it is that two sets of words have been generated by the same model (are similar) relative to the likelihood that the two sets of words have been generated by different models (are not similar).

The disclosed technical solution provides improvements in computational efficiency and accuracy of the similarity score. For instance, the methods described herein may be implemented with computational complexity of the order of $O(nd)$, where n is the number of words in the sets and d is the number of parameters in the parametric distributions. This is in contrast to alternative methods that have complexity that is quadratic either in n (e.g. $O(n^2 d)$) or in d (e.g. $O(nd^3)$).

In addition, accuracy is improved over alternative methods, at least in part, due to the fact that the methods described herein take into account the variance of the input word vectors. This is represented in the distribution(s) that are calculated for each model. In contrast, alternative methods make use only of, for instance, the mean word vector for a set of words, and do not take into account the variance across the set.

Furthermore, the methods described herein can be implemented in real-time based on any two sets of input words without requiring any training based on the words being compared. In contrast, alternative methods require a corpus of sentences to be analysed in advance, for instance, via principle component analysis (PCA). Furthermore, the methods described herein can be implemented without utilising any hyperparameters. Alternative methods require one or more hyperparameters to be fit to a supervised training set in order for their model to function. As no hyperparameters are utilised in the present application, no training is required for the embodiments described herein to work. This also eliminates the need for any labelled training data to be provided. In contrast to other real-time methods, the embodiments described herein provide improved accuracy and efficiency.

The embodiments described herein provide a clear framework for calculating semantic textual similarity that can be adapted easily to various situations due to the clear use of likelihood-based measures representing how well the respective models fit the respective sets of words. In contrast to alternative methods, no empirical adaptations are utilised to make the method work, and instead the similarity scores described herein are based on clearly justifiable likelihood distributions. This makes the methods described herein more transparent and easier to adapt to any situation (through the selection of the most appropriate distribution).

Further technical advantages are described in Appendix A.

The determination of similarity between sets of words, for instance, between sentences, is an important task in natural language processing. For instance, similarity can be utilised in human-machine interfaces, such as chatbots, by determining a response to an input set of words by comparing the words to a database of potential inputs and associating the input with the potential input that is most similar.

FIG. 1 shows a system in accordance with a first embodiment, the system comprises a user interface 1 for use by a user 3. The user interface 1 may be provided on a mobile phone, the user's computer or other device capable of hosting a web application with a voice input and transmitting a query across the internet.

The user 3 inputs a query into the interface and this is transmitted across the internet 5 to a conversation handling service 7. The conversation handling service 7 sends the query to an embedding service 9. The conversation handling service 7 may be provided with simple logic which allows the device to, for example, direct the user 3 to a human operator if required etc. The embedding service 9 generates a vector representation for the input query. The embedding service 9 generates vector representations based on machine learning models that have been trained on training data. In this case, the models are also evaluated by a medical professional.

The embedding service 9 submits the generated vector representation to a content retrieval service 11. The content retrieval service 11 reads a content database 13 and compares the vector representation of the input query, (which will be referred to hereinafter as the input vector representation) to other vector representations in the database. The content retrieval service 11 determines whether the input vector representation is similar to other vector representations within the content database 13. The content retrieval service may be implemented on a computing system comprising a processor and memory.

In an embodiment, the input vector representation determined to be similar to other vector representations, then content associated with the similar vector representations is passed back to the user 3 via the interface 1, where it is displayed. The content may be directed to the user 3 via the embedding service 9 or may be sent direct to the interface 1.

In a further embodiment, if no sufficiently similar content is in the content database, the query is passed to the content authoring service 15. The content authoring service groups similar queries into clusters. If the size of a cluster exceeds a threshold, it is determined that content for these similar queries needs to be generated. In an embodiment, this content will be generated by a medical professional 17. Once validated, the new content is added to the content database 13.

After being presented with suitable content (existing or new), the user 3 may select a "call to action" which is submitted to the conversation handling service 7. The conversation handling service may communicate with other internal services (e.g. a diagnostic engine 19) to satisfy the user request.

The present embodiment relates to an interface for handling medical queries based on content that is authored by a medical professional; however, it will be appreciated that this can equally be applied to any type of query for any type of content.

It can be seen from the above description that the effectiveness of retrieval of responses to queries depends strongly on the ability to determine the similarity between the queries and predetermined queries (that have predetermined responses) stored in the content database 13.

The embodiments described herein aim to improve the ability determine this similarity by determining the likelihood through the use of Bayesian model comparison.

Figure 2:
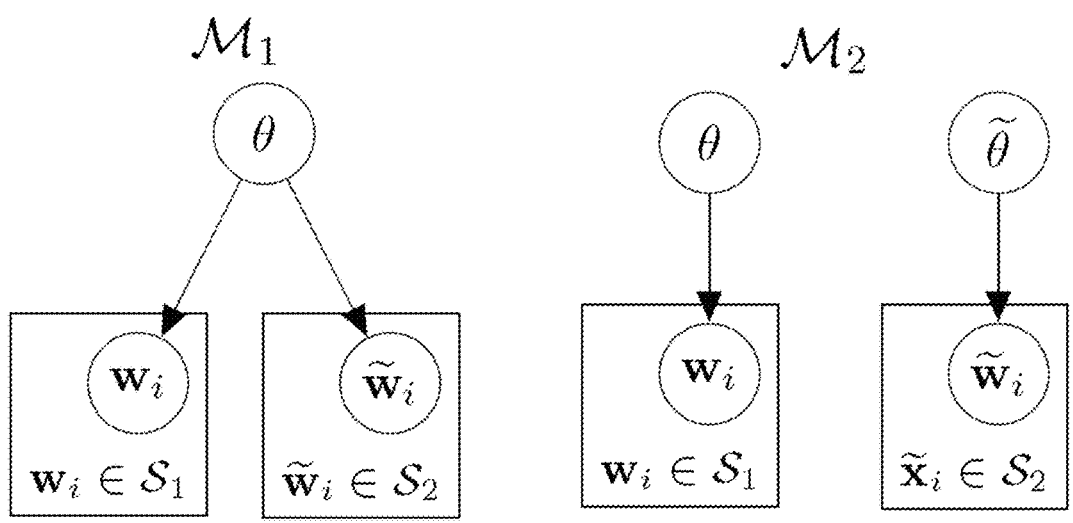
FIG. 2 is a graphical representation of two potential generative models for two sets of words in accordance with an embodiment.

FIG. 2 is a graphical representation of two potential generative models for two sets of words in accordance with an embodiment.

In the first model ($M_1$), two sets of words ($S_1$ and $S_2$) are generated from the same parametric distribution (having parameters $\theta$). $S_1$ is the set of words $w_i$ and $S_2$ is the set of words $\tilde{w}_i$. The two sets are independent and identically distributed.

In the second model ($M_2$), the two sets of words ($S_1$ and $S_2$) are generated from the distinct parametric distributions (having parameters $\theta$ and $\tilde{\theta}$, respectively). Again, the two sets are independent and identically distributed.

The above framework allows the embodiments described herein to determine the likelihood that the two sets are generated from the same parametric distribution and are therefore semantically linked/similar, or are generated from distinct parametric distributions and are therefore not semantically linked/similar.

Using the graphical models discussed above embodiments utilise a score based on Bayesian inference to compare sets $S_1$ and $S_2$:

$$sim(S_1, S_2) = \frac{p(S_1, S_2 | M_1)}{p(S_1, S_2 | M_2)} = \frac{p(S_1, S_2 | M_1)}{p(S_1 | M_2)p(S_2 | M_2)}$$

This quantity is known as the Bayes factor, which is used as the model comparison score. The score provides a ratio of the probability of the two sets being generated by the first model to the probability of the two sets being generated by the second model. That is, the score provides the ratio of the probability of the two sets being generated by the same parametric distribution compared to the probability of the two sets being generated by distinct parametric distributions.

To obtain the evidences $p(S_j|M_i)$ the parameters of the respective model ($\theta$) need to be marginalized out yielding a robust Bayesian score:

$$p(S_1, S_2 | M_1) = \int p(S_1, S_2 | \theta)p(\theta)d\theta$$

$$p(S_1, S_2 | M_1) = \int \prod_{w_k \in S_1 \cup S_2} p(w_k | \theta)p(\theta)d\theta$$

$$p(S_i | M_2) = \int \prod_{w_k \in S_i} p(w_k | \theta)p(\theta)d\theta$$

Computing the semantic score of sets $S_1$, $S_2$ then requires: selecting a reasonable model likelihood $p(w_k|\theta)$ and prior $p(\theta)$ and computing the marginal evidence scores specified above.

Figure 3:
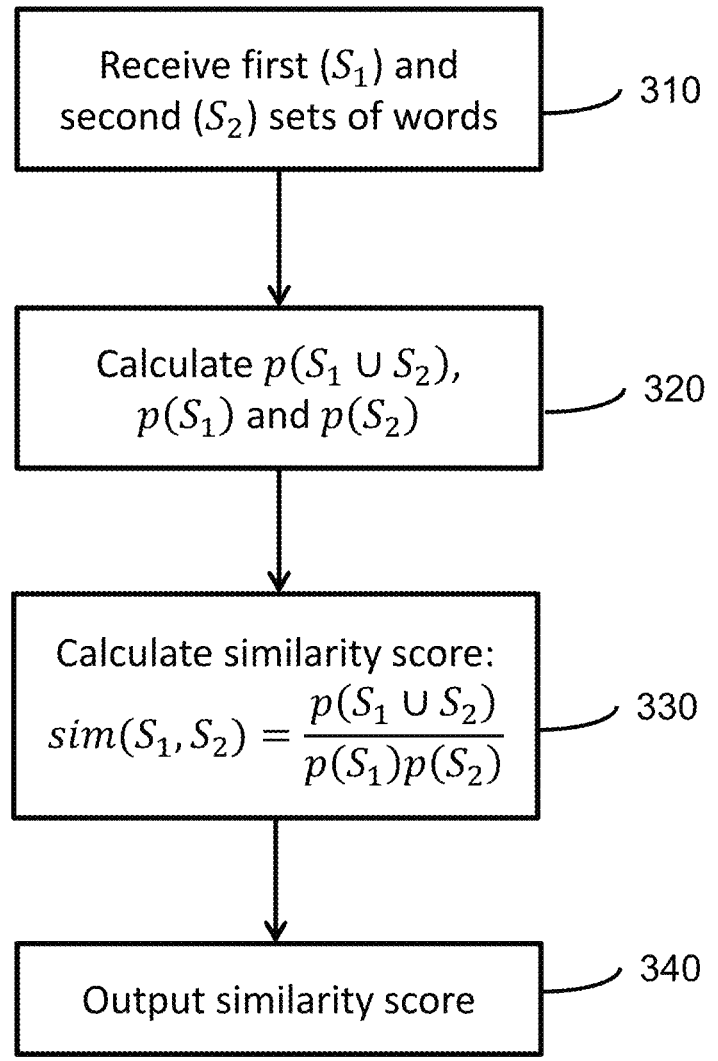
FIG. 3 shows a flow chart of a method of determining the similarity between two sets of words in accordance with an embodiment.

FIG. 3 shows a flow chart of a method 300 of determining the similarity between two sets of words in accordance with an embodiment. The method starts with the receipt 310 of a first set of words ($S_1$) and a second set of words ($S_2$). The words may be received as word embeddings (a vector mapping the word onto a lower dimensional space), or may be received as word vector (a vector mapping the word onto a space with one dimension per word) and then converted into a word embedding by the system itself. Alternatively, the method may be performed on word vectors that haven't been subject to an embedding. In the present embodiment, the embeddings of the words in the sentences are analysed as this improves the accuracy of the system by allowing the system to take into account the additional semantic meaning encoded within the embeddings.

Next, the probability of the two sets of words being generated from the same probability distribution is calculated p ($S_1 \cup S_2$) as well as the probability of each set of words being generated independently ($p(S_1)$ and $p(S_2)$) 320. These probability values are then used to determine the similarity score by dividing the probability that the two sets of words are generated from the same probability distribution by the probability that the two sets are generated from distinct probability distributions 330. The similarity score is then output 340 (e.g. for use in a dialogue system).

This embodiment can be used in semantic text similarity tasks which can be evaluated by the sentEval toolkit. A concrete application of this method would be in the setting of question answering systems when trying to retrieve the most similar sentence from a database of example sentences.

Model Complexity Penalty

The embodiments described above make use of a similarity score that is equivalent to a likelihood ratio test. In certain embodiments, a model complexity penalty is implemented within the similarity score to improve performance by preventing under- and over-fitting.

The Bayes factor can be sensitive to the choice of prior and can result in estimates that heavily under-fit the data (especially under a vague prior), having the tendency to always select the simpler model. This can be overcome by using the empirical Bayes procedure; however, a downfall to this method is the issue of double counting. This can thus be prone to over-fitting. Embodiments described herein overcome these issues by applying a test that is similar to a likelihood ratio test that does not depend on the prior and is robust to overfitting.

The different choices of likelihood and their potential implications over sentence semantics and word embeddings are also explored herein.

Information Criteria

Information criteria may be used to assess which model ($M_1$ or $M_2$) most accurately describes the sets of words. The probability for each set and each model can be approximated via an information criterion for that model and set of words:

$$\ln p(S_i, M_i) \approx IC(S_i, M_i)$$

There are multiple information criteria for model selection, each being suited to different scenarios. For instance, the Bayes Information Criterion (BIC) or the Akaiki Information Criterion (AIC) may be utilised.

Certain embodiments utilise information criteria with the general form:

$$IC(S, M) = -(\alpha \hat{\mathcal{L}} + \Omega(S, M))$$

Where $\hat{\mathcal{L}}$ is the maximised value of the log likelihood function for model M and $\Omega(S, \hat{\mathcal{L}})$ represents a model complexity penalty term which is model and information criterion (IC) specific. The model complexity penalty term helps to prevent overfitting.

Using the above general formulation for the involved information criterion, the similarity score can be derived as:

$$sim(S_1, S_2) = -IC(\{S_1, S_2\}, M_1) + IC(\{S_1, S_2\}, M_2)$$

$$sim(S_1, S_2) = \alpha(\hat{\mathcal{L}} * \hat{\theta}_{1,2} | M_1) - (\hat{\mathcal{L}}(\hat{\theta}_1 | M_2) + \hat{\mathcal{L}}(\hat{\theta}_2 | M_2))) - \Omega(\{S_1, S_2\}, M_1) + \Omega(\{S_1, S_2\}, M_2)$$

In the above equation, α is a scaling factor that is set based on the information criterion that is utilised. For instance, α is 1 for the Bayesian Information Criterion and 2 for the Akaiki Information Criterion. Equally, the computational complexity term $\Omega(S, \hat{\mathcal{L}})$ can take a variety of forms depending on the information criterion utilised.

Information Theoretic Criterion

The goal of these criteria is to evaluate the goodness of fit for a particular model specified by $\mathcal{L}(\hat{\theta}|w)$ on unseen data generated according to the true distribution G(w). These family of criterion perform this evaluation using the Kullback-Leibler (KL) divergence ($D_{KL}$) between the true model G(w) and the fitted model $\mathcal{L}(\hat{\theta}|w)$:

$$D_{KL}(G(w) \| p(w|\hat{\theta})) = \mathbb{E}_G\left[\ln \frac{G(w)}{p(w|\hat{\theta})}\right]$$

$$= H_G(w) - \mathbb{E}_G[\ln p(w|\hat{\theta})]$$

In other words, the Kullback-Leibler divergence between the true model and the fitted model is the expectation of the logarithmic distance between the probability distribution for the true model and the probability distribution for the fitted model. In the above equations, $H_G(w)$ is the entropy of the probability distribution for the true model (G(w)). The KL divergence provides a measure of the difference between the two probability distributions.

Given the entropy of the true model will be a constant quantity for different likelihoods, the quantity of interest in the definition of the information criterion is a good estimator for the expected log likelihood $\mathbb{E}_G[\ln p(w|\hat{\theta})]$. One such estimator is given by the normalized maximum likelihood. One such estimator is given by the normalized maximum likelihood:

$$\mathbb{E}_{\hat{G}}[\ln p(w|\hat{\theta})] = \frac{1}{n} \sum_{i=1}^{n} p(w_i | \hat{\theta})$$

This estimator introduces a bias that varies with respect to the dimension of the parameter vector of the model θ and requires a correction in order to carry out a fair comparison of information criteria. Such a correction is implemented in the Takeuchi Information Criterion (TIC):

$$TIC(S, M) = -2(\hat{\mathcal{L}}_M - tr(\hat{I}\hat{J}^{-1}))$$

where $\hat{J}$ is the expected Hessian (the Hessian Matrix evaluated at the maximum likelihood parameters) and $\hat{I}$ is the Fisher Information (the Fisher Information matrix evaluated at the maximum likelihood parameters):

$$\hat{J} = \frac{1}{n} \sum_{i=1}^{n} \nabla_\theta^2 \mathcal{L}(\theta|w_i)|_{\theta=\hat{\theta}}$$

$$\hat{I} = \frac{1}{n} \sum_{i=1}^{n} \nabla_\theta \mathcal{L}(\theta|w_i) \nabla_\theta \mathcal{L}^\top(\theta|w_i)|_{\theta=\hat{\theta}}$$

For the case where it is assumed that the proposed model $\mathcal{L}(\hat{\theta}|w)$ has the same parametric form as the true model, $\hat{I} = \hat{j}$ resulting in a penalty $tr(\hat{I}\hat{J}^{-1}) = tr(I_k) = k$ where k is the number of model parameters. This results in the Akaike information criterion.

Akaiki Information Criterion

The Akaiki Information Criterion (AIC) is an estimator for the relative quality of models. Based on the above, the AIC is:

$$AIC(S, M) = -2(\hat{\mathcal{L}}_M - k)$$

where $\hat{\mathcal{L}}$ is the maximised likelihood function of the model, $\hat{\mathcal{L}}_M = p(x|\hat{\theta}, M)$, where $\hat{\theta}$ are the parameters that maximise the likelihood function, x is the observed data (in this case, the words of sets $S_1$ and $S_2$, and k is the number of model parameters.

The AIC is similar to the Bayesian Information Criterion (BIC), discussed later; however, it does not directly approximate the probability p(S, M).

In one embodiment, the value for AIC for the respective model and set of words can be utilised as an approximation for the probability p(S, M).

The AIC simplification of TIC relies on several assumptions that only hold true in the big data limit and rely on assuming the estimated model M has the same parametric form as the true model. In general TIC is a more robust approximation. This is especially that case where the datasets are sentences and thus the number of samples is small.

This specific information criterion provides the following similarity score:

$$sim(S_1, S_2) = \alpha(\mathcal{L}(\hat{\theta}_{1,2}|M_1) - (\mathcal{L}(\hat{\theta}_1|M_2) + \mathcal{L}(\hat{\theta}_2|M_2))) - tr(\hat{I}_{1,2}\hat{J}_{1,2}^{-1}) + (tr(\hat{I}_1\hat{J}_1^{-1}) + tr(\hat{I}_2\hat{J}_2^{-1}))$$

This is determined by subtracting the Takeuchi Information Criterion (TIC) for the second model ($M_2$) from the TIC for the first model ($M_1$).

The above similarity score can be computed using Algorithm 1 below.

---

Algorithm 1 Calculate sim ($S_1$, $S_2$)

1:    input: Sentences $S_1 := \{w_{le}\}_{le=1}^m$, $S_2 = \{\tilde{w}_k\}_{k=1}^l$
2:    Compute the maximum likelihood estimates under the 2 models:
      $\hat{\theta}_{1,2} := \arg\max_\theta \mathcal{L}(\theta|S_1 \cup S_2)$
      $\hat{\theta}_1 := \arg\max_\theta \mathcal{L}(\theta|S_1)$ and $\hat{\theta}_2 := \arg\max_\theta \mathcal{L}(\theta|S_2)$
3:    Calculate the grad vector and Hessian for each model:
      $\nabla_{\theta_1}\mathcal{L}(\theta|w)$, $\nabla_{\theta_2}\mathcal{L}(\theta|w)$, $\nabla_{\theta_{1,2}}\mathcal{L}(\theta|w)$
      $\nabla_{\theta_1}^2\mathcal{L}(\theta|w)$, $\nabla_{\theta_2}^2\mathcal{L}(\theta|w)$, $\nabla_{\theta_{1,2}}^2\mathcal{L}(\theta|w)$
4:
      sim ($S_1$, $S_2$) := $\alpha$ ($\hat{\mathcal{L}}(\hat{\theta}_{1,2}|M_1) - (\hat{\mathcal{L}}(\hat{\theta}_1|M_2) + (\hat{\mathcal{L}}(\hat{\theta}_2|M_2))) -$
          tr ($\hat{I}_{1,2}\hat{J}_{1,2}^{-1}$) + (tr ($\hat{I}_1\hat{J}_1^{-1}$) + tr ($\hat{I}_2\hat{J}_2^{-1}$))
5:    output: sim ($S_1$, $S_2$)

---

Figure 4:
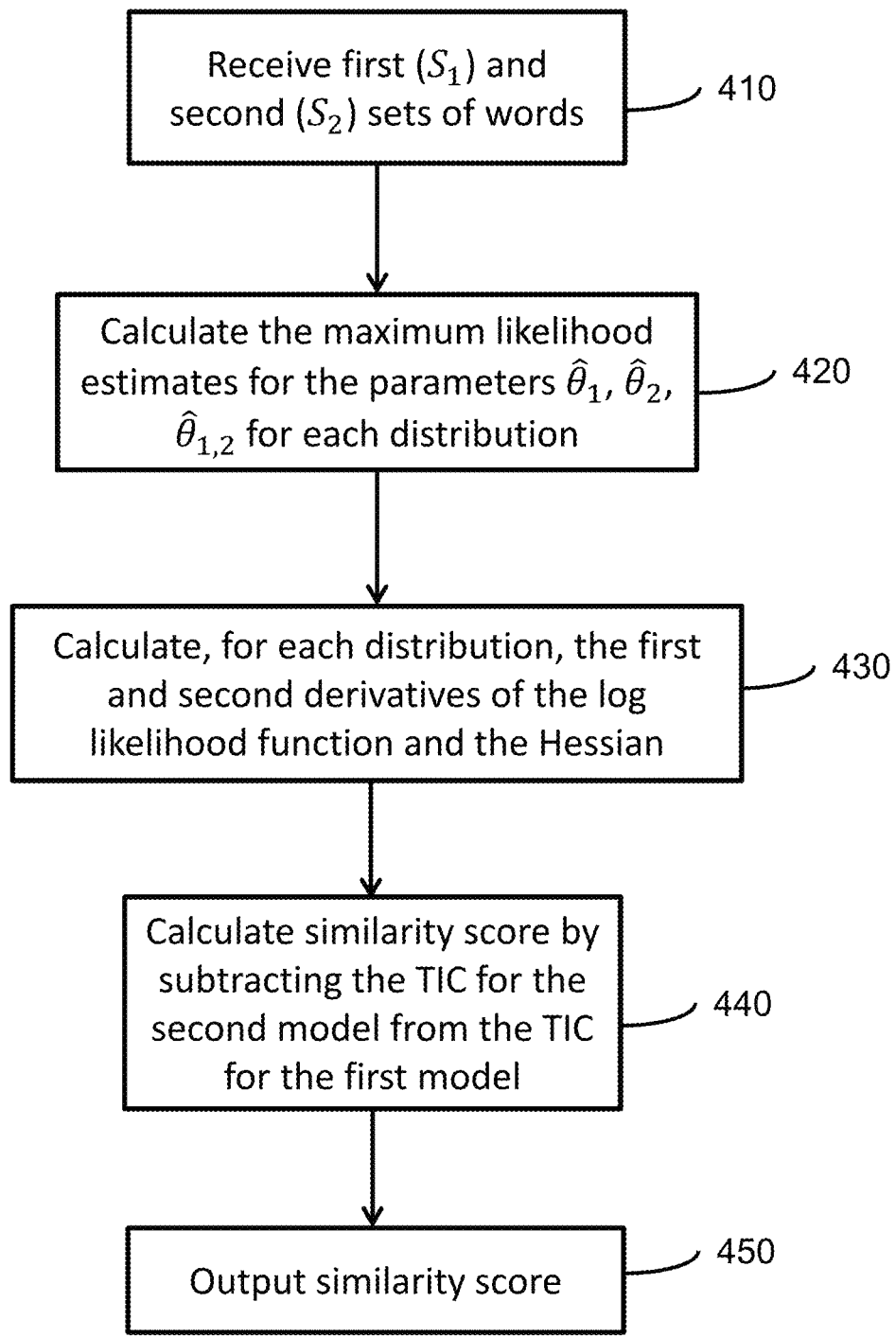
FIG. 4 shows a method of calculating the similarity score based on the Takeuchi Information Criterion (TIC) according to an embodiment.

FIG. 4 shows a method of calculating the similarity score based on the Takeuchi Information Criterion (TIC) according to an embodiment. This represents the method of Algorithm 1.

The method 400 starts with the receipt of the first and second sets of words 410. The maximum likelihood estimates for the parameters under each model are then determined 420. This is achieved by determining the parameters for each distribution that maximise the likelihood function for that distribution based on the respective set of words. That is, the parameters that maximise the likelihood of those words being generated by the respective distribution.

Accordingly, for the first model (which models the two sets of words via a single distribution), the parameters $\hat{\theta}_{1,2}$ are determined that maximise the likelihood of the given distribution generating both sets of words ($S_1$ and $S_2$). For the second model (which models the two sets of words via two independent distributions), the parameters for each distribution $\hat{\theta}_1$ and $\hat{\theta}_2$ are determined that maximise the likelihood of the respective distribution producing the respective set of words ($S_1$ and $S_2$ respectively).

The maximum likelihood estimates are utilised to determine the information criterion for the respective model. The similarity score is then based on the relative size of the two information criterion. In the present embodiment, the information criterion being utilised is the Takeuchi Information Criterion (TIC). As discussed above, this makes use of the Hessian $\hat{J}$ and the Fisher Information $\hat{I}$.

In light of the above, step 430 involves the calculation of the first and second derivatives of the log likelihood function for each distribution. This allows the calculation of the Hessian $\hat{J}$ and Fisher Information $\hat{I}$. These values are calculated for use in the calculation of the TIC for each model.

The similarity score 440 is then determined based on the TIC for the first model relative to the TIC for the second model. As the present embodiment operates in the logarithmic domain, this is determined by subtracting the TIC for the second model from the TIC from the first model.

The similarity score is then output 450.

Von Mises-Fisher Likelihood

Word embeddings are traditionally learned by optimizing a dot product between target words and context vectors. Due to the latter, cosine similarity is used to measure the semantic similarity of words in various information retrieval tasks. Accordingly, in one embodiment the embeddings are models as vectors lying on the surface of a d−1 dimensional unit hyper-sphere $S_1, S_2 \subseteq \mathbb{S}^{d-1}$ distributed (i.i.d) according to a von Mises-Fisher (vMF) likelihood:

$$p(S|\mu, \kappa) = \left(\frac{1}{Z(\kappa)^n}\right)\prod_{i=1}^n \exp(\kappa\mu^\top w_i)$$

$$p(S|\mu, \kappa) = \left(\frac{\kappa^{\frac{d}{2}-1}}{(2\pi)^{\frac{d}{2}}I_{\frac{d}{2}-1}(\kappa)}\right)^n \prod_{i=1}^n \exp(\kappa\mu^\top w_i)$$

where $\mu$ is the mean direction vector K is the concentration parameter, with supports $\|\mu\| = \|w_i\| = 1$, $\kappa \geq 0$. $I_\upsilon(\kappa)$ corresponds to a modified Bessel function of the first kind with order $\upsilon$.

The random variable is parameterised to polar hyperspherical $w_i(\phi)(\phi = (\phi_1, \ldots, \phi_{d-1})^T)$:

$$p(\phi|\theta, \kappa) = \left(\frac{\kappa^{\frac{d}{2}-1}}{(2\pi)^{\frac{d}{2}}I_{\frac{d}{2}-1}(\kappa)}\right)\left|\frac{\partial w_i}{\partial \phi}\right|\exp(\kappa\mu(\theta)^\top w(\phi))$$

where:

$$w_i(\phi) = ((1 - \delta_{id})\cos(\phi_i) + \delta_{id})\prod_{k=1}^{i-1}\sin(\phi_k)$$

$$\mu_i(\theta) = ((1 - \delta_{id})\cos(\theta_i) + \delta_{id})\prod_{k=1}^{i-1}\sin(\theta_k)$$

$$\left|\frac{\partial w}{\partial \phi}\right| = \prod_{k=1}^{d-2}\sin(\phi_k)^{d-k-1}$$

This reparametrisation simplifies the calculation of the Hessian and the empirical Fisher information matrix. The maxima of the likelihood remains unchanged since $$\left|\frac{\partial w}{\partial \phi}\right|$$

does not depend on $\theta$, thus the maximum likelihood estimate (MLE) in the polar coordinates parametrisation is given by applying the map from the Cartesian MLE to polar coordinates $\hat{\theta} = \mu^{-1}(\hat{\mu})$.

The gradient and Hessian of the vMF log likelihood are given by:

$$\frac{\partial}{\partial \theta_k}\mathcal{L}(\theta, \kappa|\phi) = \kappa\sum_{j=k}^d w_j(\phi)\mu_j(\theta)((1 - \delta_{kj})\cot\theta_k - \delta_{kj}\tan\theta_k)$$

-continued $$\frac{\partial^2}{\partial^2 \theta_k} \mathcal{L}(\theta, \kappa \mid \phi) = -\kappa \sum_{j=k}^{d} w_j(\phi)\mu_j(\theta)$$

$$\frac{\partial^2}{\partial \theta_l \partial \theta_k} \mathcal{L}(\theta, \kappa \mid \phi) = \kappa \sum_{j=max(k,l)}^{d} w_j(\phi) \frac{\frac{\partial}{\partial \theta_k}\mu_j(\theta)\frac{\partial}{\partial \theta_l}\mu_j(\theta)}{\mu_j(\theta)}$$

$$\frac{\partial}{\partial \kappa} \mathcal{L}(\theta, \kappa \mid \phi) = \mu(\theta)^\top w(\phi) - \frac{I_{\frac{d}{2}}(\kappa)}{I_{\frac{d}{2}-1}(\kappa)}$$

$$\frac{\partial^2}{\partial \kappa \partial \phi_k} \mathcal{L}(\theta, \kappa \mid \phi) = \kappa^{-1}\frac{\partial \mathcal{L}(\theta, \kappa \mid \phi)}{\partial \theta_k}$$

$$\frac{\partial^2}{\partial \kappa^2} \mathcal{L}(\theta, \kappa \mid \phi) =$$

$$\frac{I_{\frac{d}{2}}(\kappa)\left(I_{\frac{d}{2}-2}(\kappa) + I_{\frac{d}{2}}(\kappa)\right) - I_{\frac{d}{2}-1}(\kappa)\left(I_{\frac{d}{2}-1}(\kappa) + I_{\frac{d}{2}+1}(\kappa)\right)}{2I_{\frac{d}{2}-1}(\kappa)^2}$$

Further embodiments and additional technical advantages are described in Appendix A.

Computing System

Figure 5:
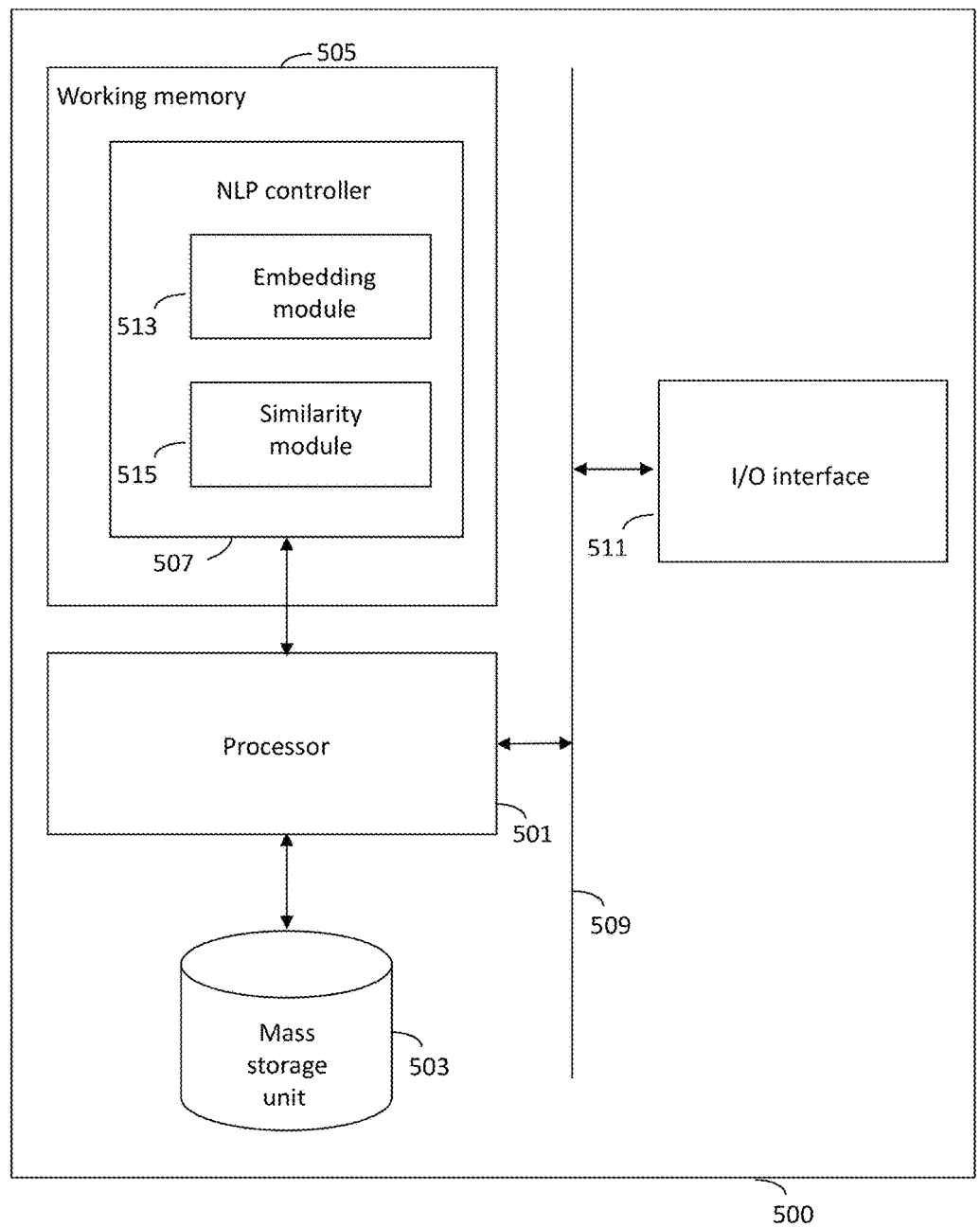
FIG. 5 shows means capable of putting an embodiment, as described herein, into effect.

While the reader will appreciate that the above embodiments are applicable to any commuting system to determine similarity between sets of words, a typical computing system is illustrated in FIG. 5, which provides means capable of putting an embodiment, as described herein, into effect. As illustrated, the computing system 500 comprises a processor 501 coupled to a mass storage unit 503 and accessing a working memory 505. As illustrated, a natural language processing (NLP) controller 507 is represented as a software product stored in working memory 505. However, it will be appreciated that elements of the NLP controller 507 may, for convenience, be stored in the mass storage unit 503.

Usual procedures for the loading of software into memory and the storage of data in the mass storage unit 503 apply. The processor 501 also accesses, via bus 509, an input/output interface 511 that is configured to receive data from and output data to an external system (e.g. an external network or a user input or output device). The input/output interface 511 may be a single component or may be divided into a separate input interface and a separate output interface.

The NLP controller 507 includes an embedding module 513 and a similarity module 515. The embedding module 513 is operable to retrieve the sets of words for comparison and determine embedding vectors for the words (for instance, by multiplying word vectors for the words with an embedding matrix). The similarity module 515 is configured to determine the similarity between two sets of embedded vectors using the methods described herein. Thus, execution of the NLP software 507 by the processor 501 will cause embodiments as described herein to be implemented.

The NLP controller software 507 can be embedded in original equipment, or can be provided, as a whole or in part, after manufacture. For instance, the NLP controller software 507 can be introduced, as a whole, as a computer program product, which may be in the form of a download, or to be introduced via a computer program storage medium, such as an optical disk. Alternatively, modifications to an existing NLP controller 507 can be made by an update, or plug-in, to provide features of the above described embodiment.

The computing system 500 may be an end-user system that receives inputs from a user (e.g. via a keyboard) and determines similarity values (e.g. for determining a response to a query). Alternatively, the system may be a server that receives input over a network and determines the similarity values. Either way, these similarity values may be used to determine appropriate responses to user queries, as discussed with regard to FIG. 1.

For instance, the mass storage unit may store predefined phrases, and the system may be configured to determine similarity values with respect to an input phrase relative to each of the predefined phrases. The system may then be able to determine the most similar predefined phrase and then respond with a predefined response that is associated with that predefined phrase. The predefined phrases may be stored as sets of embedding vectors.

Accordingly, by providing more accurate and efficient means of determining the similarity between sets of words, the embodiments described herein provide improvements in natural language processing that, for instance, can improve the accuracy and efficiency of artificial conversational entities.

Whilst the embodiment of FIG. 7 includes an embedding module, alternative embodiments may receive embeddings for each word as an input. This may be the case where a separate system calculates the embedding vectors and provides these to the system for calculating the similarity between sets of embedding vectors.

Implementations of the subject matter and the operations described in this specification can be realized in digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

While certain arrangements have been described, the arrangements have been presented by way of example only, and are not intended to limit the scope of protection. The inventive concepts described herein may be implemented in a variety of other forms. In addition, various omissions, substitutions and changes to the specific implementations described herein may be made without departing from the scope of protection defined in the following claims.

The invention claimed is:

1. A computer-implemented method for natural language processing for a human-machine interface through statistical model comparison, comprising:

receiving a first set of words and a second set of words;
calculating a first likelihood-based measure representing how well a first model can be fit to the first and second sets of words, the first model comprising a shared parametric distribution representing both the first and second sets of words;
calculating a second likelihood-based measure representing how well a second model can be fit to the first and second sets of words, the second model comprising a first parametric distribution representing the first set of words and a second parametric distribution representing the second set of words;
calculating a similarity score based on a ratio of the first likelihood measure to the second likelihood measure, the similarity score being representative of the similarity between the first and second sets of words;
outputting the similarity score to the human-machine interface to determine a semantic similarity between the first set of words and the second set of words; and
associating, through the human-machine interface, the first set of words with the second set of words based on the semantic similarity to determine a response.

2. The method of claim 1 wherein the first, second and shared parametric distributions are first, second and shared likelihood functions respectively, each defined by a respective set of parameters.

3. The method of claim 2 wherein the first and second sets of words are first and second sets of word embeddings constrained to lie on the surface of a unit hypersphere, and wherein the first, second and shared likelihood functions are in accordance with the von Mises-Fisher distribution.

4. The method of claim 2 further comprising determining maximum likelihood estimates for the parameters for each likelihood function.

5. The method of claim 4 wherein the first likelihood-based measure is calculated based on a maximum value for the shared likelihood function and the second likelihood-based measure is calculated based on maximum values for the first and second likelihood functions.

6. The method of claim 5 wherein the first and second information criteria are in accordance with the Takeuchi Information Criterion or the Akaiki Information Criterion.

7. The method of claim 1 wherein the first and second likelihood based measures are first and second information criteria respectively.

8. The method of claim 1 wherein the first and second likelihood-based measures each comprise a respective penalty based on complexity for the respective model.

9. A system for natural language processing for a human-machine interface through statistical model comparison comprising one or more processors configured to:
receive a first set of words and a second set of words;
calculate a first likelihood-based measure representing how well a first model can be fit to the first and second sets of words, the first model comprising a shared parametric distribution representing both the first and second sets of words;
calculate a second likelihood-based measure representing how well a second model can be fit to the first and second sets of words, the second model comprising a first parametric distribution representing the first set of words and a second parametric distribution representing the second set of words;
calculate a similarity score based on a ratio of the first likelihood measure to the second likelihood measure, the similarity score being representative of the similarity between the first and second sets of words;
output the similarity score to the human-machine interface to determine a semantic similarity between the first set of words and the second set of words; and
associate, through the human-machine interface, the first set of words with the second set of words based on the semantic similarity to determine a response.

10. The system of claim 9 wherein the first, second and shared parametric distributions are first, second and shared likelihood functions respectively, each defined by a respective set of parameters.

11. The system of claim 10 wherein the first and second sets of words are first and second sets of word embeddings constrained to lie on the surface of a unit hypersphere, and wherein the first, second and shared likelihood functions are in accordance with the von Mises-Fisher distribution.

12. The system of claim 10 wherein the one or more processors are further configured to determine maximum likelihood estimates for the parameters for each likelihood function.

13. The system of claim 12 wherein the first likelihood-based measure is calculated based on a maximum value for the shared likelihood function and the second likelihood-based measure is calculated based on respective maximum values for the first and second likelihood functions.

14. The system of claim 9 wherein the first and second likelihood based measures are first and second information criteria respectively.

15. The system of claim 14 wherein the first and second information criteria are in accordance with the Takeuchi Information Criterion or the Akaiki Information Criterion.

16. The system of claim 9 wherein the first and second likelihood-based measures each comprise a respective penalty based on complexity for the respective model.

17. A non-transient computer readable medium containing programming instructions for natural language processing for a human-machine interface through statistical model comparison that, when executed by a computer, cause the computer to:
receive a first set of words and a second set of words;
calculate a first likelihood-based measure representing how well a first model can be fit to the first and second sets of words, the first model comprising a shared parametric distribution representing both the first and second sets of words;
calculate a second likelihood-based measure representing how well a second model can be fit to the first and second sets of words, the second model comprising a first parametric distribution representing the first set of words and a second parametric distribution representing the second set of words;
calculate a similarity score based on a ratio of the first likelihood measure to the second likelihood measure, the similarity score being representative of the similarity between the first and second sets of words;
output the similarity score to the human-machine interface to determine a semantic similarity between the first set of words and the second set of words; and
associate, through the human-machine interface, the first set of words with the second set of words based on the semantic similarity to determine a response.

* * * * *